US012565479B2

(12) United States Patent
Kim et al.

(10) Patent No.: US 12,565,479 B2
(45) Date of Patent: Mar. 3, 2026

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Chi-Sik Kim, Gyeonggi-do (KR); Soo-Yong Lee, Gyeonggi-do (KR); Seung-Hoon Yoo, Gyeonggi-do (KR); Dong-Hyung Lee, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 0 days.

(21) Appl. No.: 18/493,118

(22) Filed: Oct. 24, 2023

(65) Prior Publication Data

US 2024/0067618 A1 Feb. 29, 2024

Related U.S. Application Data

(63) Continuation of application No. 17/287,951, filed as application No. PCT/KR2019/014150 on Oct. 25, 2019, now abandoned.

(30) Foreign Application Priority Data

Oct. 26, 2018 (KR) ........................ 10-2018-0129371
Oct. 24, 2019 (KR) ........................ 10-2019-0132727

(51) Int. Cl.
*C07D 307/91* (2006.01)
*C07D 405/10* (2006.01)
(Continued)

(52) U.S. Cl.
CPC ......... *C07D 307/91* (2013.01); *C07D 405/10* (2013.01); *C07D 407/10* (2013.01);
(Continued)

(58) Field of Classification Search
None
See application file for complete search history.

(56) References Cited

U.S. PATENT DOCUMENTS

2018/0123055 A1* 5/2018 Park ..................... C07D 495/04
2020/0111974 A1* 4/2020 Nakano ................ H10K 85/615
2023/0042023 A1 2/2023 Tasaki et al.

FOREIGN PATENT DOCUMENTS

WO WO-2016/171429 A2 * 10/2016
WO 2019235902 A1 12/2019
WO 2020060359 A1 3/2020

OTHER PUBLICATIONS

Search Report from KIPO for Korean Patent Application No. 10-2023-0057132; Application Date: May 2, 2023.
(Continued)

*Primary Examiner* — Jay Yang
(74) *Attorney, Agent, or Firm* — G. Creston Campbell

(57) ABSTRACT

The present disclosure relates to an organic electroluminescent compound and an organic electroluminescent device comprising the same. The organic electroluminescent compound of the present disclosure may be comprised in a light-emitting layer, and is effective for producing an organic electroluminescent device having high luminescent efficiency and/or excellent lifespan characteristic.

5 Claims, 1 Drawing Sheet

(51) Int. Cl.
*C07D 407/10* (2006.01)
*C07D 513/04* (2006.01)
*H10K 85/60* (2023.01)
*H10K 50/11* (2023.01)

(52) U.S. Cl.
CPC ......... *C07D 513/04* (2013.01); *H10K 85/626* (2023.02); *H10K 85/6572* (2023.02); *H10K 85/6574* (2023.02); *H10K 85/6576* (2023.02); *H10K 50/11* (2023.02)

(56) References Cited

OTHER PUBLICATIONS

Cited Reference from Japanl Patent Office for Japan patent application No. 2024-000844; Application Date: Jan. 5, 2024.

* cited by examiner

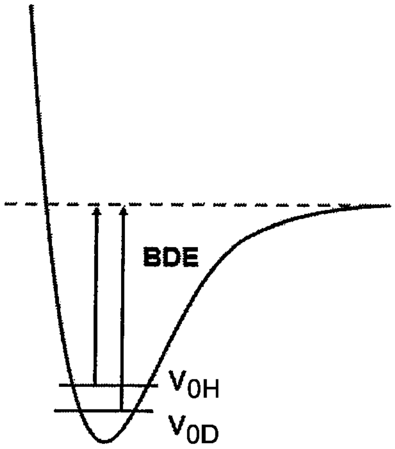
BDE
V0H
V0D

ORGANIC ELECTROLUMINESCENT COMPOUND AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 17/287,951, filed Apr. 22, 2021, which is the National Stage Entry Of PCT/KR2019/014150, filed Oct. 25, 2019, both of which are incorporated by reference herein in their entirety.

TECHNICAL FIELD

The present disclosure relates to an organic electroluminescent compound and an organic electroluminescent device comprising the same.

BACKGROUND ART

An electroluminescent (EL) device is a self-light-emitting device which has advantages in that it provides a wider viewing angle, a greater contrast ratio, and a faster response time. An organic EL device was first developed by Eastman Kodak in 1987, by using small aromatic diamine molecules and aluminum complexes as materials for forming a light-emitting layer [Appl. Phys. Lett. 51, 913, 1987].

An organic electroluminescent device (OLED) changes electric energy into light by applying electricity to an organic light-emitting material, and commonly comprises an anode, a cathode, and an organic layer formed between the two electrodes. The organic layer of the OLED may comprise a hole injection layer, a hole transport layer, a hole auxiliary layer, a light-emitting auxiliary layer, an electron blocking layer, a light-emitting layer (containing host and dopant materials), an electron buffer layer, a hole blocking layer, an electron transport layer, an electron injection layer, etc. The materials used in the organic layer can be classified into a hole injection material, a hole transport material, a hole auxiliary material, a light-emitting auxiliary material, an electron blocking material, a light-emitting material, an electron buffer material, a hole blocking material, an electron transport material, an electron injection material, etc., depending on functions. In the OLED, due to an application of a voltage, holes are injected from the anode to the light-emitting layer, electrons are injected from the cathode to the light-emitting layer, and excitons of high energies are formed by a recombination of the holes and the electrons. By this energy, organic luminescent compounds reach an excited state, and light emission occurs by emitting light from energy due to the excited state of the organic luminescent compounds returning to a ground state.

Recently, according to larger area of displays, light-emitting materials which can exhibit more delicate and vivid colors are required. Specifically, in the case of blue light-emitting materials, materials such as ADN and DPVBi are used as a host material, and materials such as aromatic amine-based compounds, copper phthalocyanine compounds, carbazole-based derivatives, perylene-based derivatives, coumarin-based derivatives, and pyrene-based derivatives are used as a dopant material. However, these materials are difficult to obtain a deep blue color with high color purity, and are problematic due to having shorter light-emitting lifespan as the wavelength gets shorter.

Accordingly, in realizing a full color display, developments of light-emitting materials of deep blue having long lifespan and other organic materials having a suitable energy level with the blue light-emitting material are required.

U.S. Pat. No. 8,759,818 and U.S. Patent Application Publication No. 2014/0001459 disclose an organic electroluminescent compound comprising an anthracene moiety in which some hydrogen atoms are substituted with deuterium. However, these references do not specifically disclose an organic electroluminescent compound comprising an anthracene moiety in which some hydrogen atoms are substituted with deuterium, and wherein a dibenzofuran is substituted in a certain position.

DISCLOSURE OF INVENTION

Technical Problems

The objective of the present disclosure is firstly, to provide an organic electroluminescent compound effective for producing an organic electroluminescent device having excellent lifespan characteristic, and secondly, to provide an organic electroluminescent device comprising the organic electroluminescent compound.

Solution to Problem

In an organic electroluminescent device, an improvement of a blue light-emitting material or blue light-emitting device is important. However, from the beginning of the time when organic electroluminescent device was developed, there was no change in using a compound having a main moiety of anthracene as a blue host material. Thus, there was a limit in improving lifespan characteristics of a blue light-emitting material or blue light-emitting device. In order to improve the lifespan characteristic, the stability of an anthracene compound comprised in the blue host material can be increased. One of the methods is deuteration. When deuterating an anthracene compound, the zero point vibration energy of the compound can be lowered, thereby increasing the bond dissociation energy (BDE) of the compound. Thus, the stability of the anthracene compound can be increased. The FIGURE is a graph showing the increase of the bond dissociation energy due to deuteration. Specifically, the present inventors found that when deuterating the organic electroluminescent compound having a specific structure of the following formula 1, a more noticeable improvement in lifespan results compared to anthracene compounds having other structures. By bonding a heteroaryl instead of an aryl to an anthracene core, the mobilities of holes and/or electrons can be improved, thereby decreasing the driving voltage.

(1)

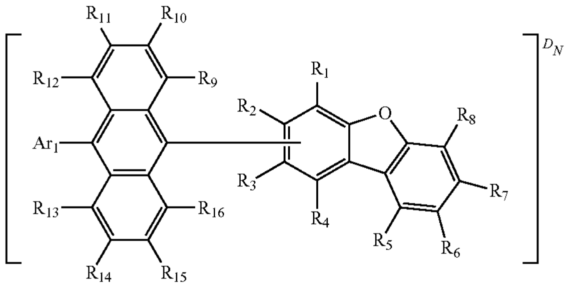

wherein $R_1$ to $R_8$ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl, with a proviso that one of $R_2$ to $R_4$ is bonded to

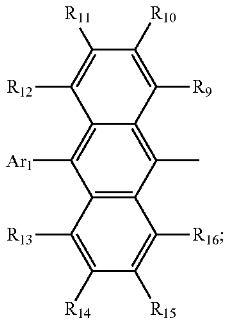

$R_9$ to $R_{16}$ each independently represent hydrogen or deuterium;

$Ar_1$ represents a substituted or unsubstituted (C6-C30) aryl, or a substituted or unsubstituted (5- to 30-membered) heteroaryl;

$D_N$ means that N hydrogen atoms are substituted with deuterium; and

N represents an integer of 8 to 50.

Advantageous Effects of Invention

By using the organic electroluminescent compound according to the present disclosure, it is possible to produce an organic electroluminescent device having improved blue light-emitting lifespan.

BRIEF DESCRIPTION OF THE FIGURE

The FIGURE is a graph illustrating an increase of the bond dissociation energy due to deuteration.

MODE FOR THE INVENTION

Hereinafter, the present disclosure will be described in detail. However, the following description is intended to explain the invention, and is not meant in any way to restrict the scope of the invention.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, an electron injection material, etc.

The organic electroluminescent material of the present disclosure may comprise at least one compound represented by formula 1. The compound represented by formula 1 may be comprised in a light-emitting layer or a hole transport layer, but is not limited thereto. For example, when comprised in a light-emitting layer, the compound represented by formula 1 may be comprised as a host such as a host for blue light-emission. According to one embodiment of the present disclosure, the compound of formula 1 may be a fluorescent host, for example, a fluorescent host for blue light-emission.

Hereinafter, the compound represented by formula 1 will be described in more detail.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl" is meant to be a monocyclic or fused ring radical derived from an aromatic hydrocarbon having 6 to 30 ring backbone carbon atoms, in which the number of the ring backbone carbon atoms is preferably 6 to 25, more preferably 6 to 18. The above aryl may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl , 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenylyl, 4"-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, a 9,9-diphenyl-1-fluorenyl, 9,9-diphenyl-2-fluorenyl, 9,9-diphenyl-3-fluorenyl, 9,9-diphenyl-4-fluorenyl, etc.

Herein, the term "(3- to 30-membered)heteroaryl" is an aryl group having 3 to 30 ring backbone atoms, and including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl such as benzofuranyl, benzothiophenyl, isobenzofuranyl, dibenzofuranyl, dibenzothiophenyl, benzonaphthofuranyl, benzonaphthothiophenyl, benzimidazolyl, benzothiazolyl, naphthothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, etc. More specifically, the heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1 -isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, a 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1 -silafluorenyl, 2-silafluorenyl, 3-silafluorenyl, 4-silafluorenyl, 1 -germafluorenyl, 2-germafluorenyl, 3-germafluorenyl, 4-germafluorenyl, etc. "Halogen" includes F, Cl, Br, and I.

In addition, "ortho (o-)," "meta (m-)," and "para (p-)" are prefixes, which represent the relative positions of substituents, respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. The substituents of the substituted alkyl, the substituted aryl, and the substituted heteroaryl in $R_1$ to $R_8$, and $Ar_1$ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30) alkyl(s) and a (3- to 30-membered)heteroaryl(s); a tri(C1-C30)alkylsilyl; a tri(C6-C30)arylsilyl; a di(C1-C30)alkyl (C6-C30)arylsilyl; a (C1-C30)alkyldi(C6-C30)arylsilyl; an amino; a mono- or di-(C1-C30)alkylamino; a mono- or di-(C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl (C6-C30)aryl. According to one embodiment of the present disclosure, the substituents each independently are at least one selected from the group consisting of a (C1-C6)alkyl, a (C6-C15)aryl, and a (5- to 15-membered)heteroaryl. Specifically, the substituents each independently may be at least one selected from the group consisting of a methyl, a phenyl, a naphthyl, a biphenyl, and a carbazolyl.

The compound represented by formula 1 may be represented by any one of the following formulas 1-1 to 1-3:

(1-1)

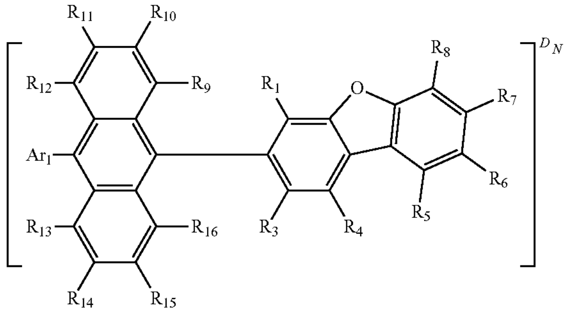

(1-2)

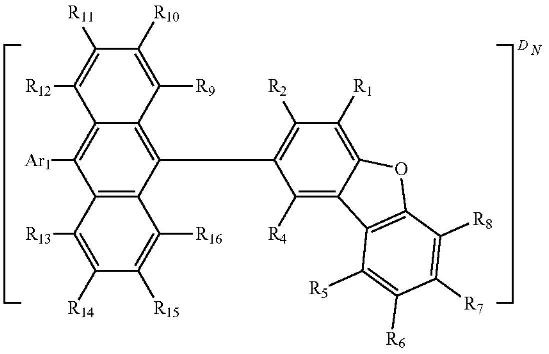

(1-3)

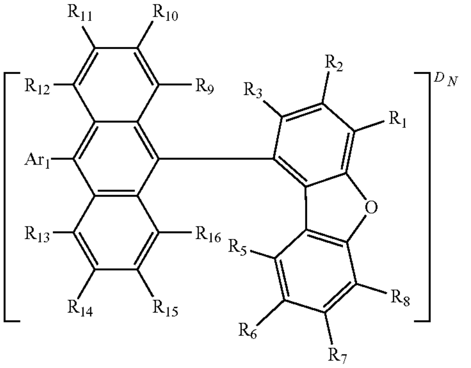

wherein $R_1$ to $R_8$, $R_9$ to $R_{16}$, $Ar_1$, and $D_N$ are as defined in formula 1, and N represents an integer of 8 to 30.

In formula 1, $R_1$ to $R_8$ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl, with a proviso that one of $R_2$ to $R_4$ is bonded to

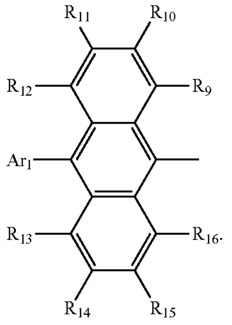

In one embodiment of the present disclosure, one of $R_2$ to $R_4$ is bonded to

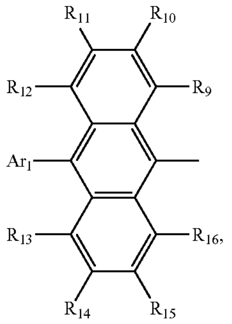

and the others of $R_2$ to $R_4$, $R_1$, and $R_5$ to $R_8$ each independently represent hydrogen or deuterium.

In formula 1, $Ar_1$ represents a substituted or unsubstituted (C6-C30)aryl, or a substituted or unsubstituted (5- to 30-membered)heteroaryl. In one embodiment of the present disclosure, $Ar_1$ represents a substituted or unsubstituted (C6-C25)aryl, or a substituted or unsubstituted (5- to 20-membered)heteroaryl. In another embodiment of the present disclosure, $Ar_1$ represents a (C6-C25)aryl unsubstituted or substituted with at least one of a (C1-C6)alkyl(s), a (C6-C15)aryl(s), and a (5- to 15-membered)heteroaryl(s); or a (5- to 20-membered)heteroaryl unsubstituted or substituted with a (C6-C12)aryl(s). Specifically, $Ar_1$ may represent a phenyl, a naphthyl, a biphenyl, a terphenyl, a phenanthrenyl, a naphthylphenyl, a phenylnaphthyl, a binaphthyl, a biphenylnaphthyl, a dimethylfluorenyl, a dimethylbenzofluorenyl, a carbazolylphenyl, a carbazolylnaphthyl, a phenylbenzothiazolyl, a phenylbenzooxazolyl, a dibenzothiophenyl, a phenylcarbazolyl, a phenylnaphthothiazolyl, a benzonaphthofuranyl, a phenylbenzocarbazolyl, a 19-membered nitrogen-containing heteroaryl, etc.

In formula 1, $D_N$ means that N hydrogen atoms in formula 1 are substituted with deuterium. N represents an integer of 8 to 50, preferably an integer of 8 to 40, more preferably an integer of 8 to 30, and even more preferably an integer of 13 to 30. When deuterated in the number of the lower limit or higher, the increase of the bond dissociation energy according to deuteration is sufficient to provide a noticeable increase in lifespan characteristics. The upper limit is determined according to the number of hydrogen atoms which can be substituted in each compound.

In one embodiment of the present disclosure, in formula 1, $R_1$ to $R_8$ which are not bonded to

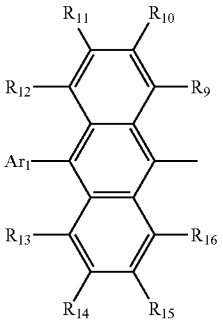

each independently represent hydrogen or deuterium; and $Ar_1$ represents a substituted or unsubstituted (C6-C25)aryl, or a substituted or unsubstituted (5- to 20-membered)heteroaryl.

In another embodiment of the present disclosure, in formula 1, $R_1$ to $R_8$ which are not bonded to

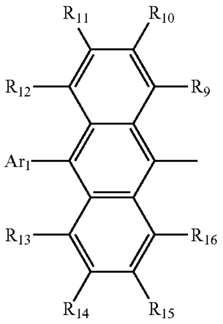

each independently represent hydrogen or deuterium; and $Ar_1$ represents a (C6-C25)aryl unsubstituted or substituted with at least one of a (C1-C6)alkyl(s), a (C6-C15)aryl(s), and a (5- to 15-membered)heteroaryl(s); or a (5- to 20-membered)heteroaryl unsubstituted or substituted with a (C6-C12)aryl(s).

In the formulas of the present disclosure, if adjacent substituents are linked to each other to form a ring, the ring may be a substituted or unsubstituted mono- or polycyclic (3- to 30-membered) alicyclic or aromatic ring, or the combination thereof, in which the formed ring may contain at least one heteroatom selected from B, N, O, S, Si, and P, preferably N, O, and S. According to one embodiment of the present disclosure, the number of the ring backbone atoms may be 5 to 20. According to another embodiment of the present disclosure, the number of the ring backbone atoms may be 5 to 15. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, the heteroaryl, each independently, may contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 includes the following compounds, but is not limited thereto.

C-1

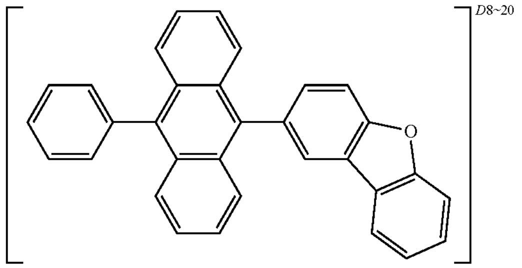

C-2

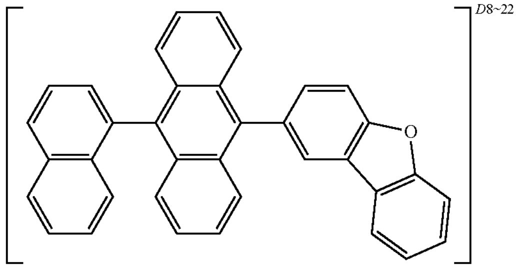

C-3

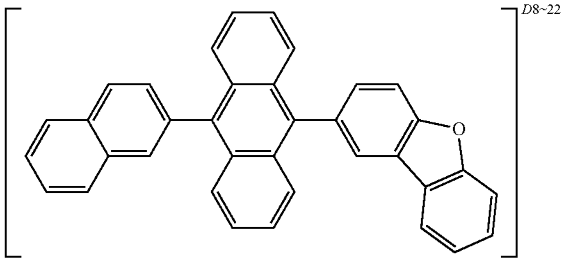

C-4

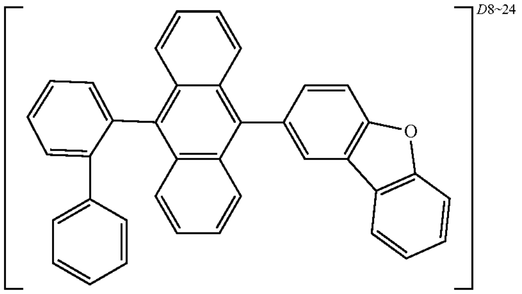

-continued
C-5
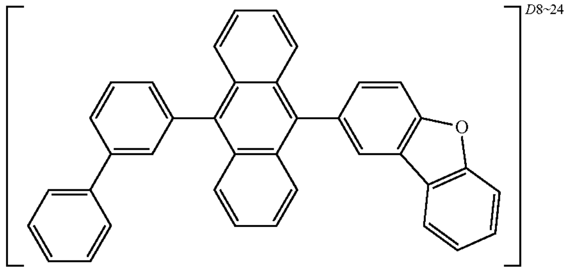
C-6
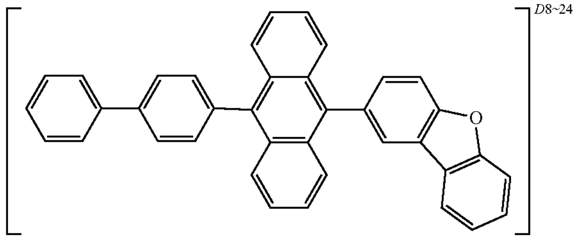
C-7
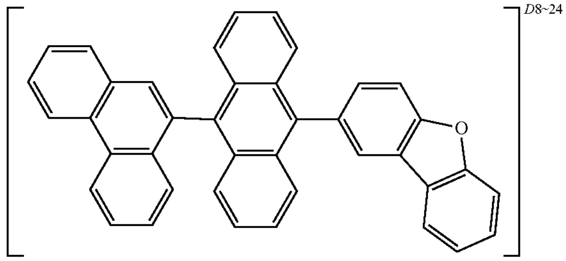
C-8
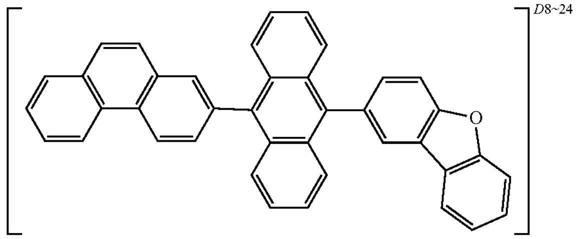
C-9
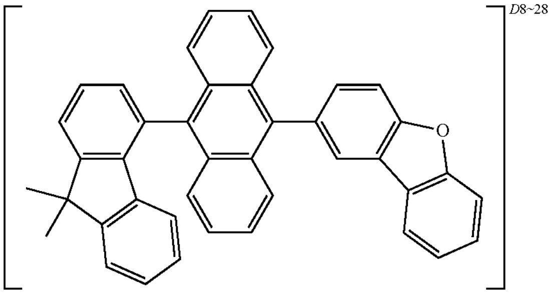
-continued
C-10
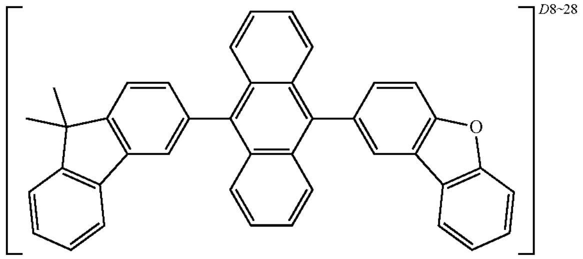
C-11
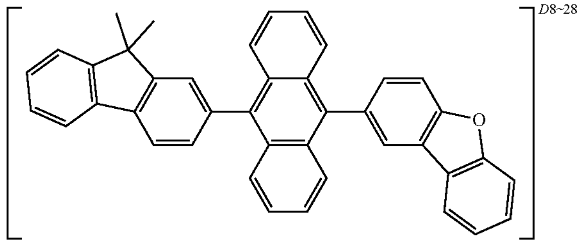
C-12
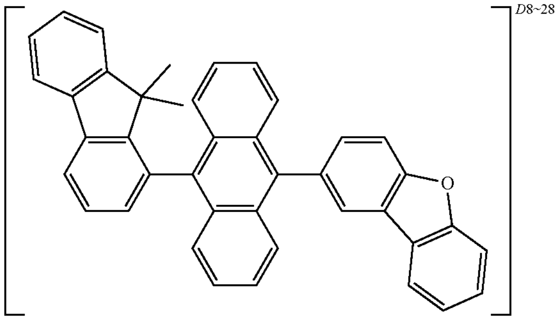
C-13
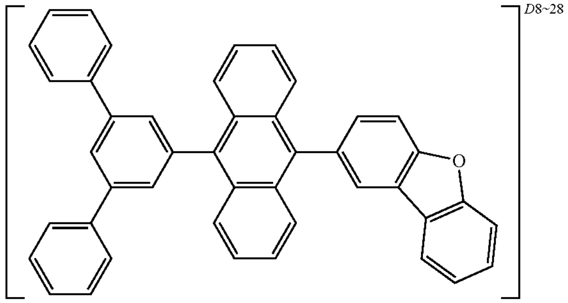
C-14
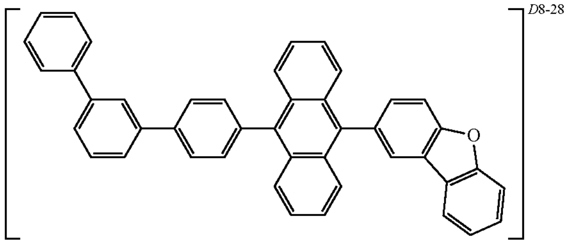

-continued
C-15
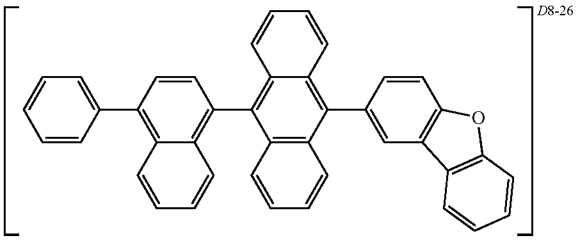
C-16
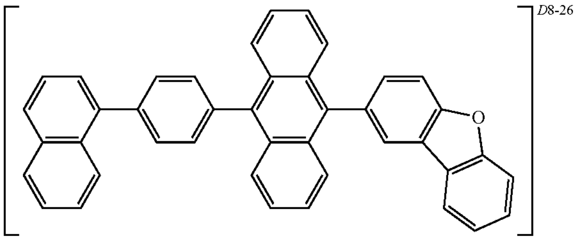
C-17
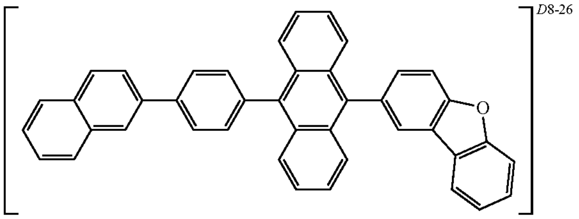
C-18
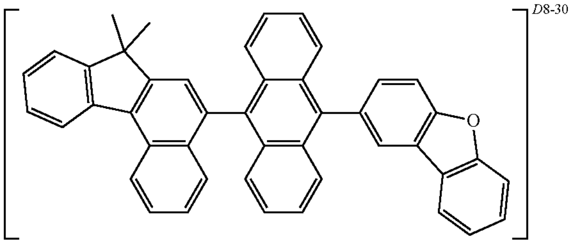
C-19
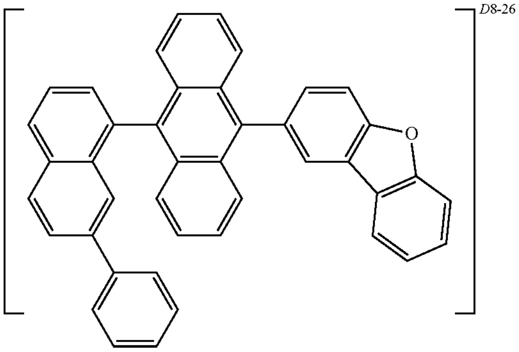
-continued
C-20
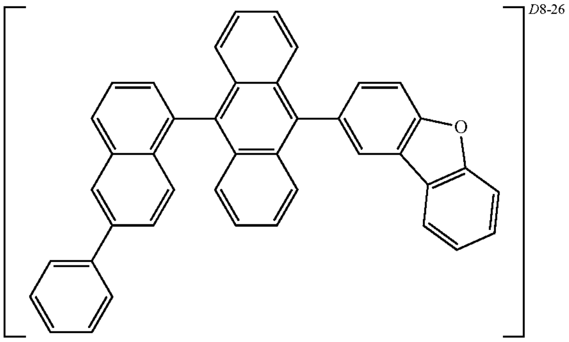
C-21
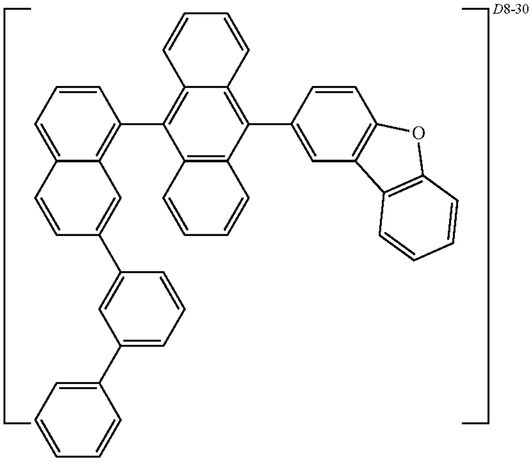
C-22
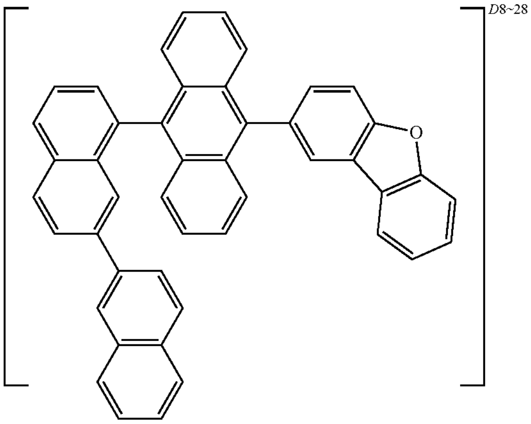
C-23
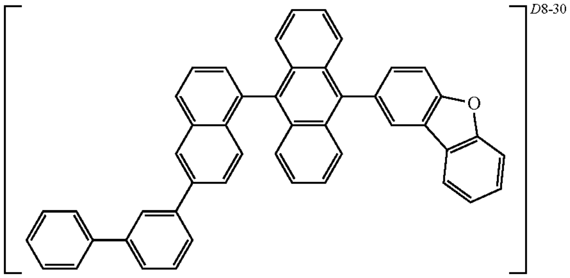

-continued
C-24
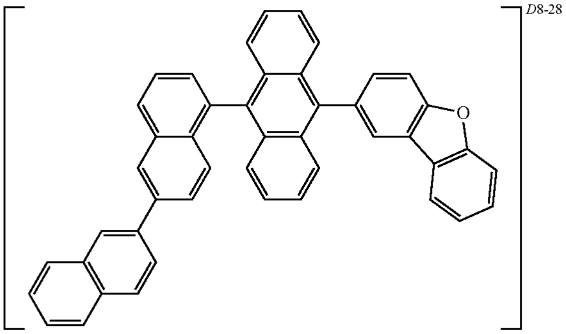
C-25
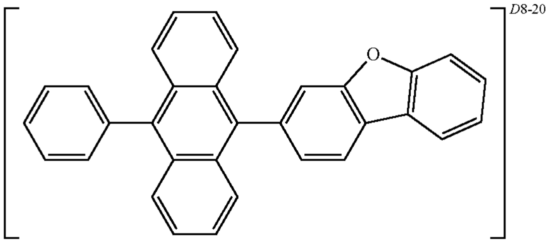
C-26
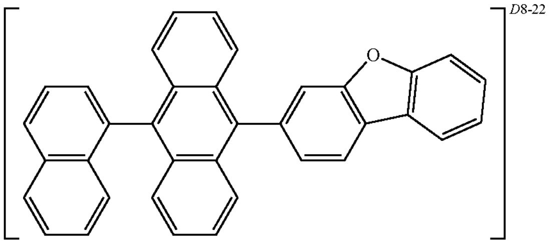
C-27
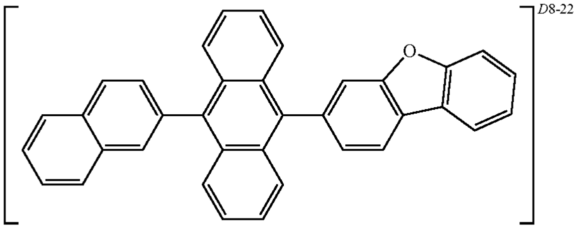
C-28
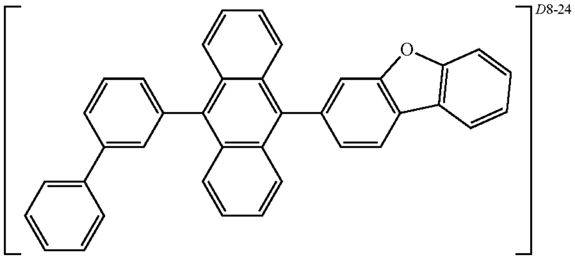
-continued
C-29
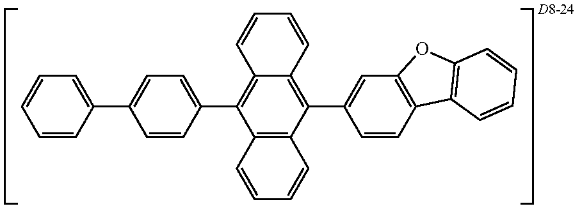
C-30
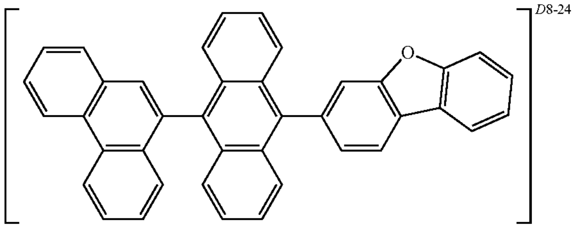
C-31
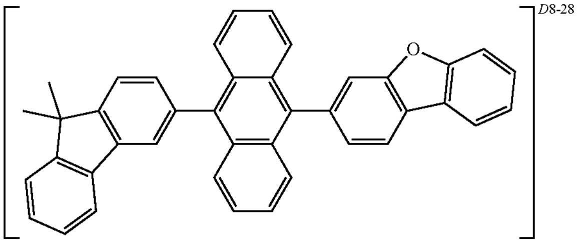
C-32
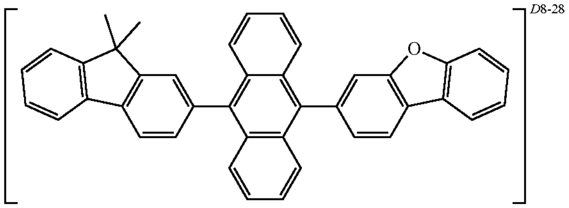
C-33
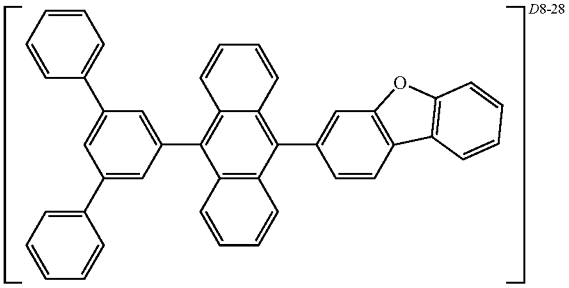
C-34
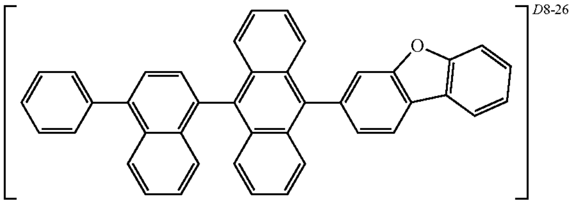

-continued
C-35
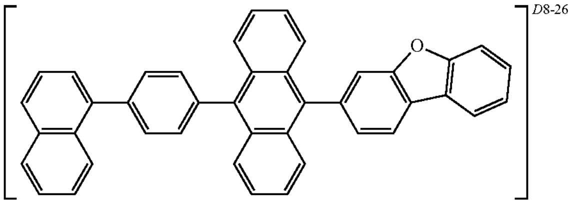
C-36
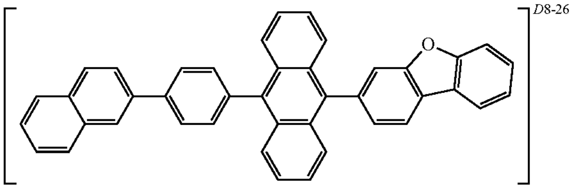
C-37
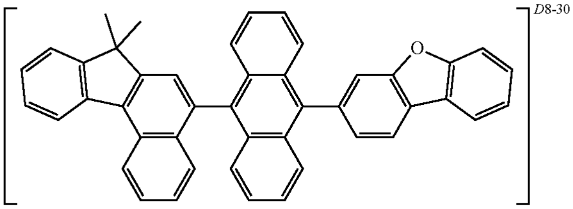
C-38
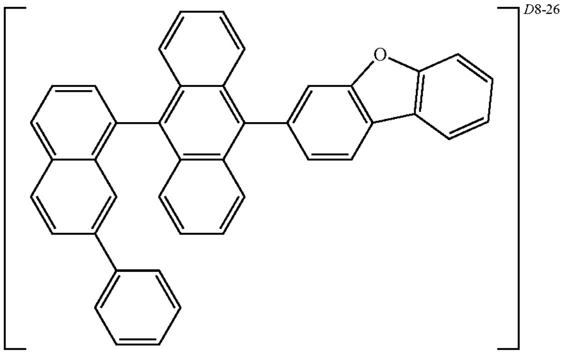
C-39
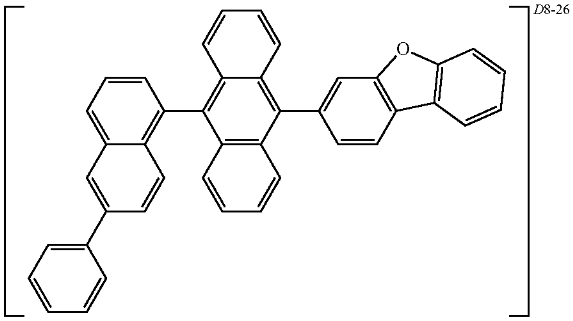
-continued
C-40
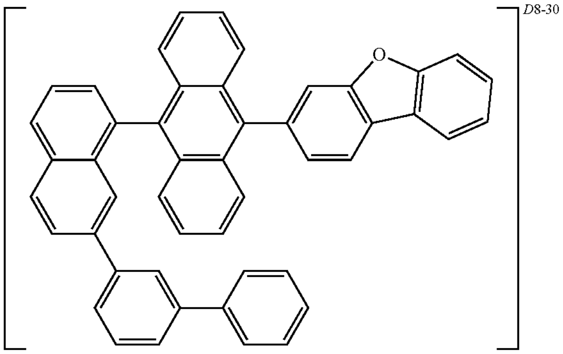
C-41
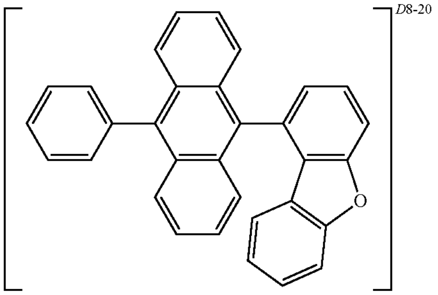
C-42
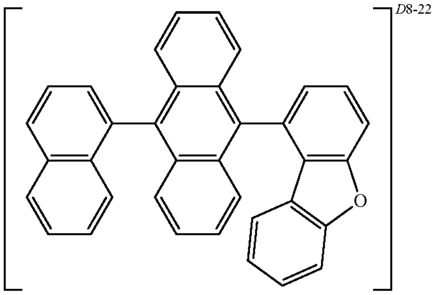
C-43
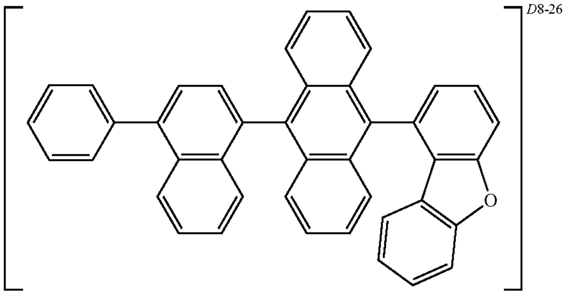
C-44
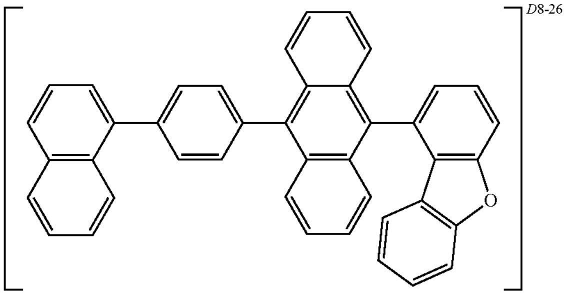

-continued
C-45
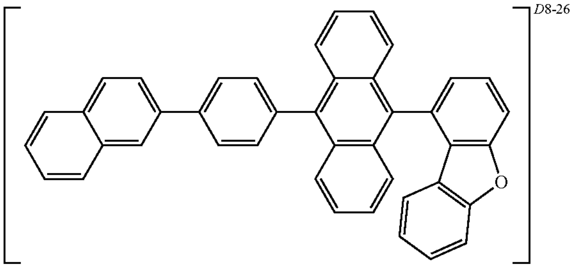
C-46
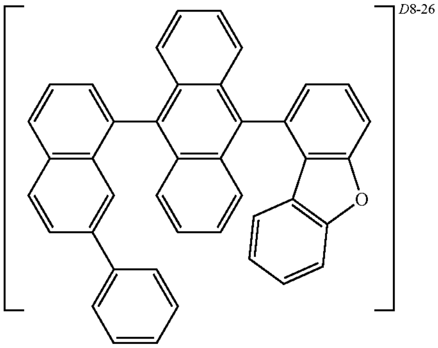
C-47
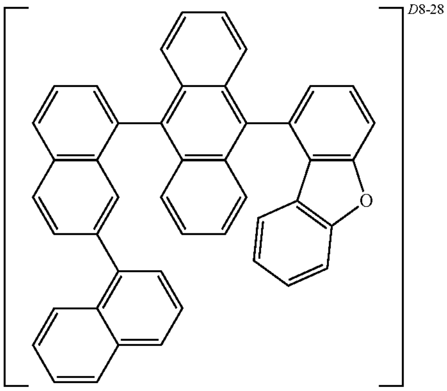
C-48
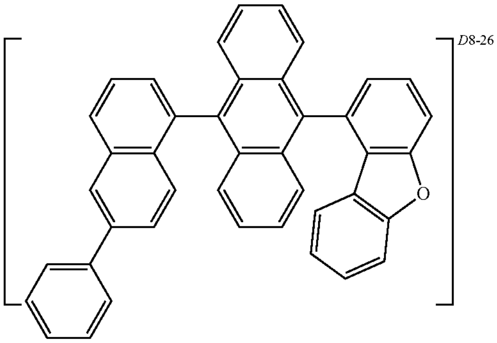
-continued
C-49
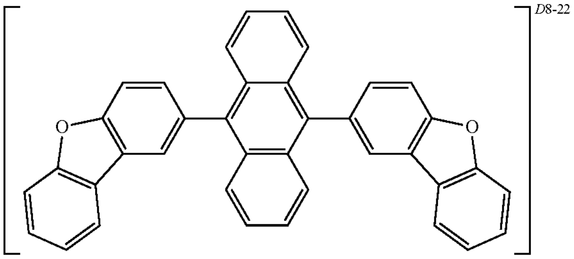
C-50
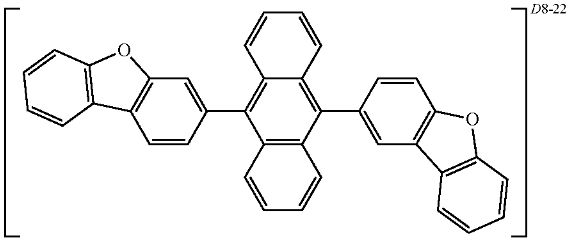
C-51
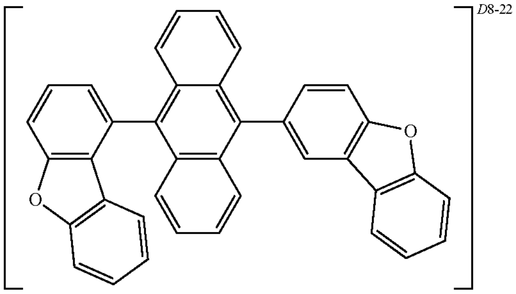
C-52
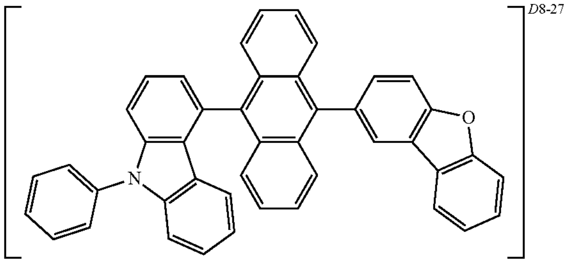
C-53
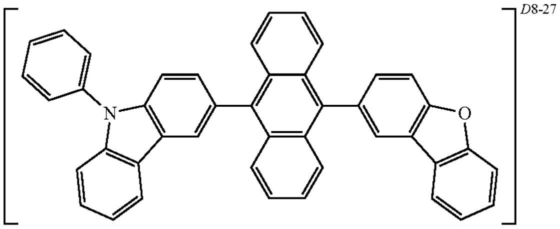

-continued
C-54
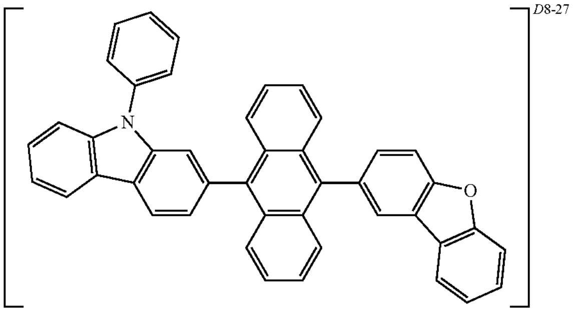
C-55
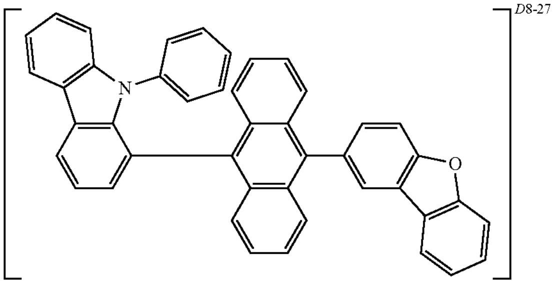
C-56
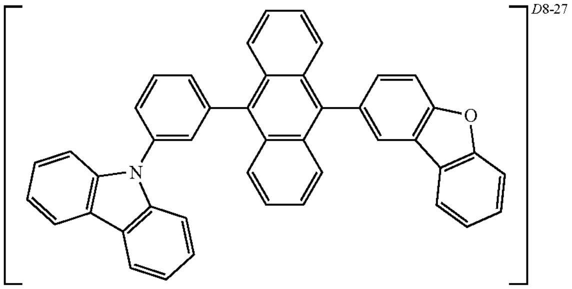
C-57
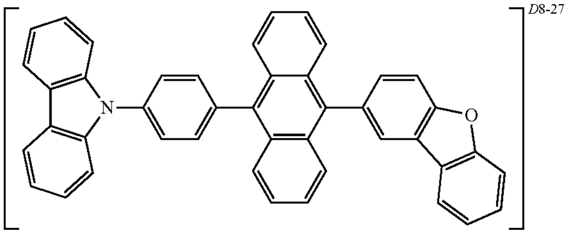
C-58
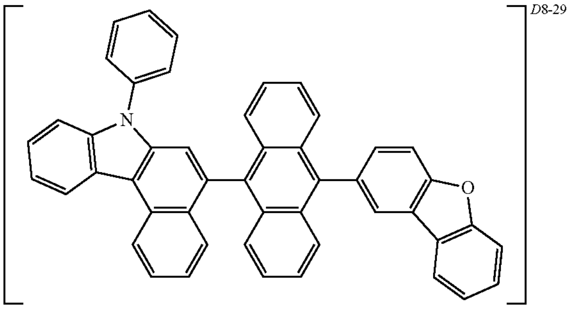
-continued
C-59
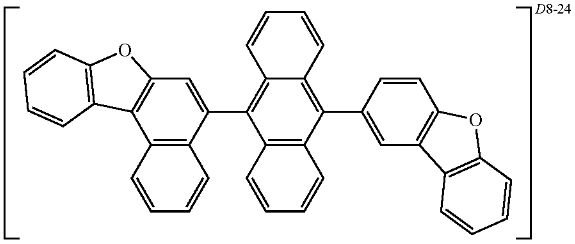
C-60
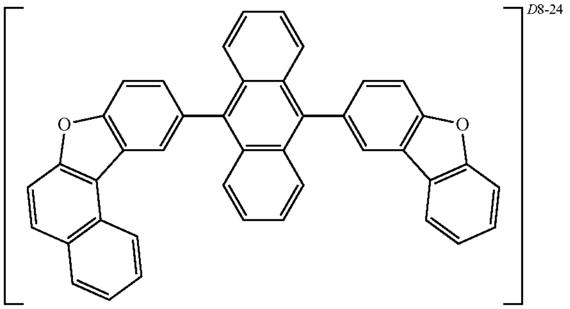
C-61
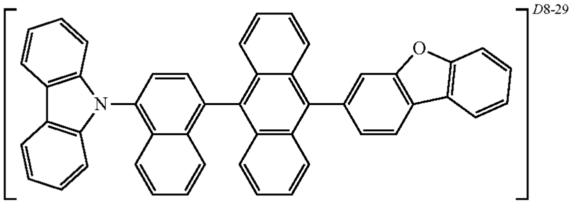
C-62
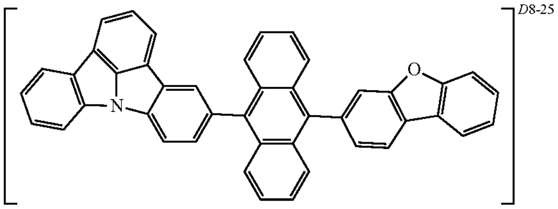
C-63
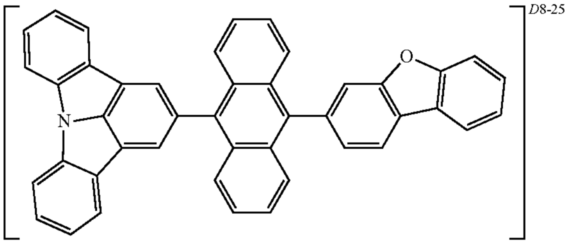
C-64
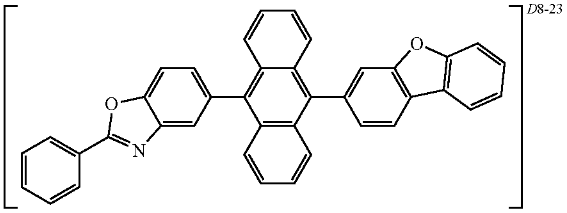

-continued
C-65
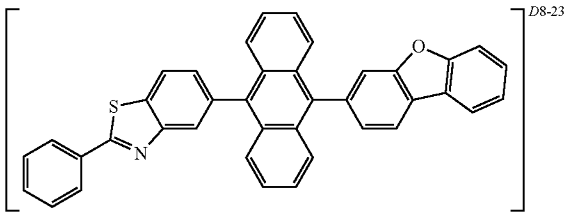
C-66
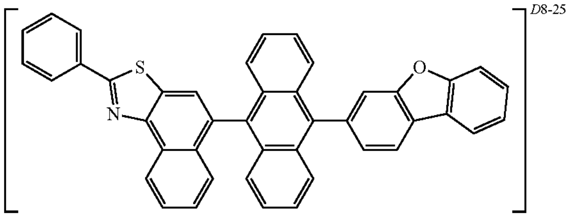
C-67
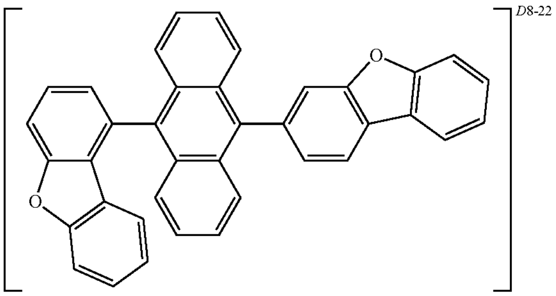
The compound of formula 1 according to the present disclosure may be prepared by a synthetic method known to one skilled in the art, and for example, as shown in the following reaction schemes, but is not limited thereto.
[Reaction Scheme 1]
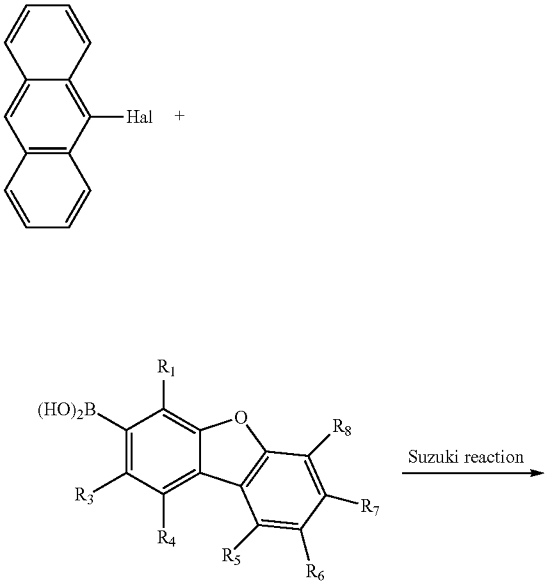
-continued
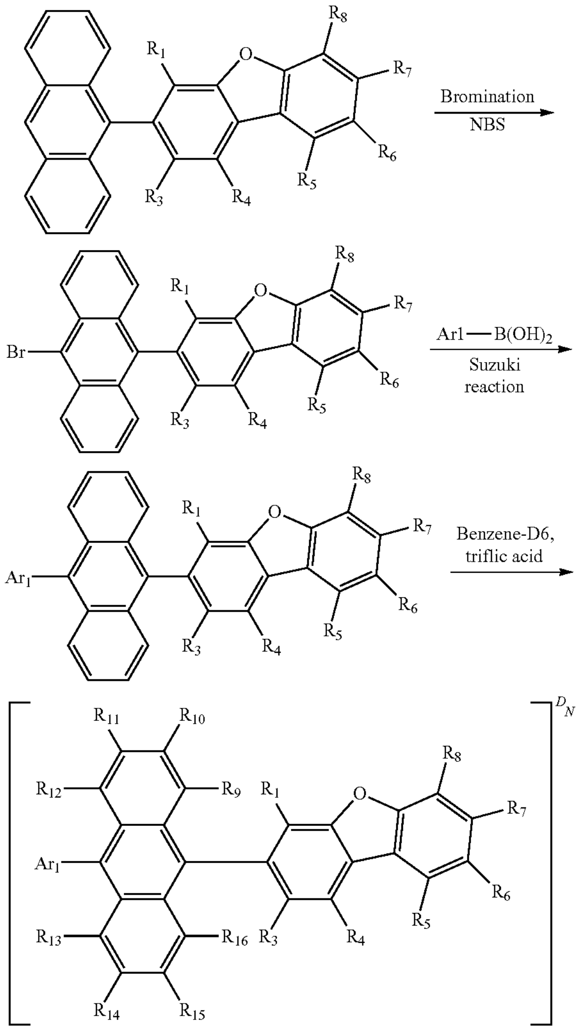
[Reaction Scheme 2]
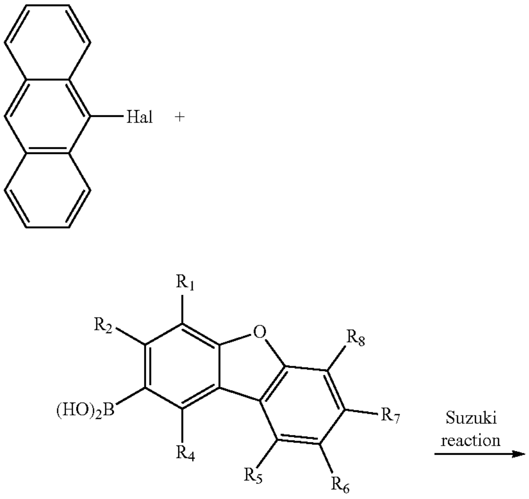

-continued
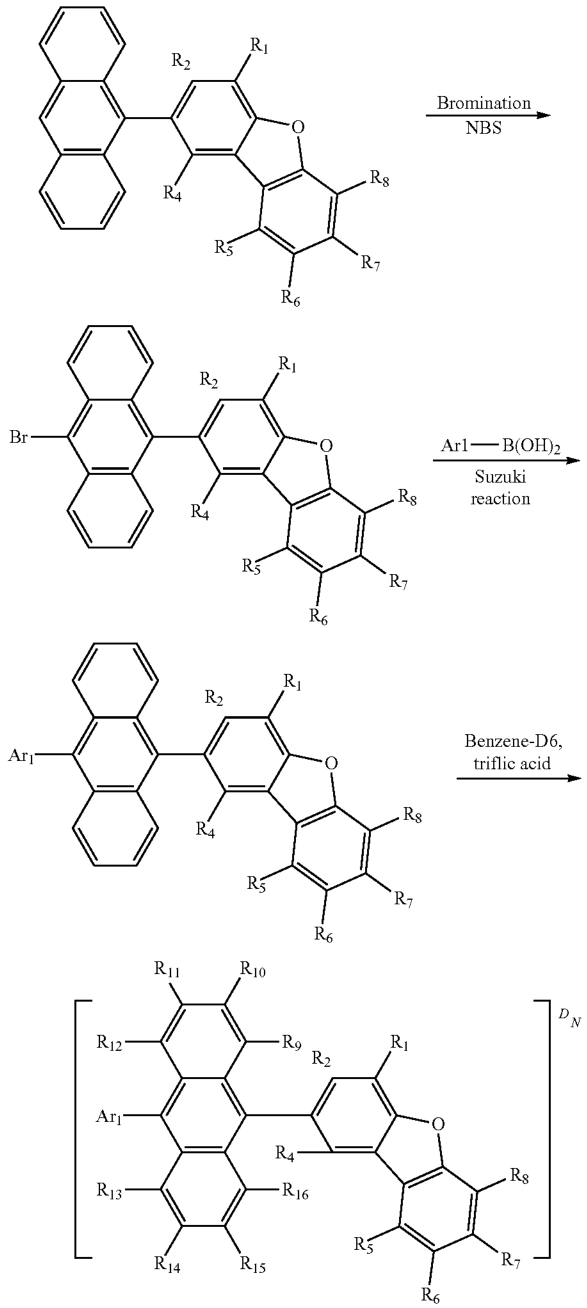
[Reaction Scheme 3]
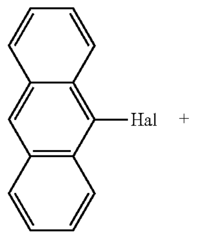
-continued
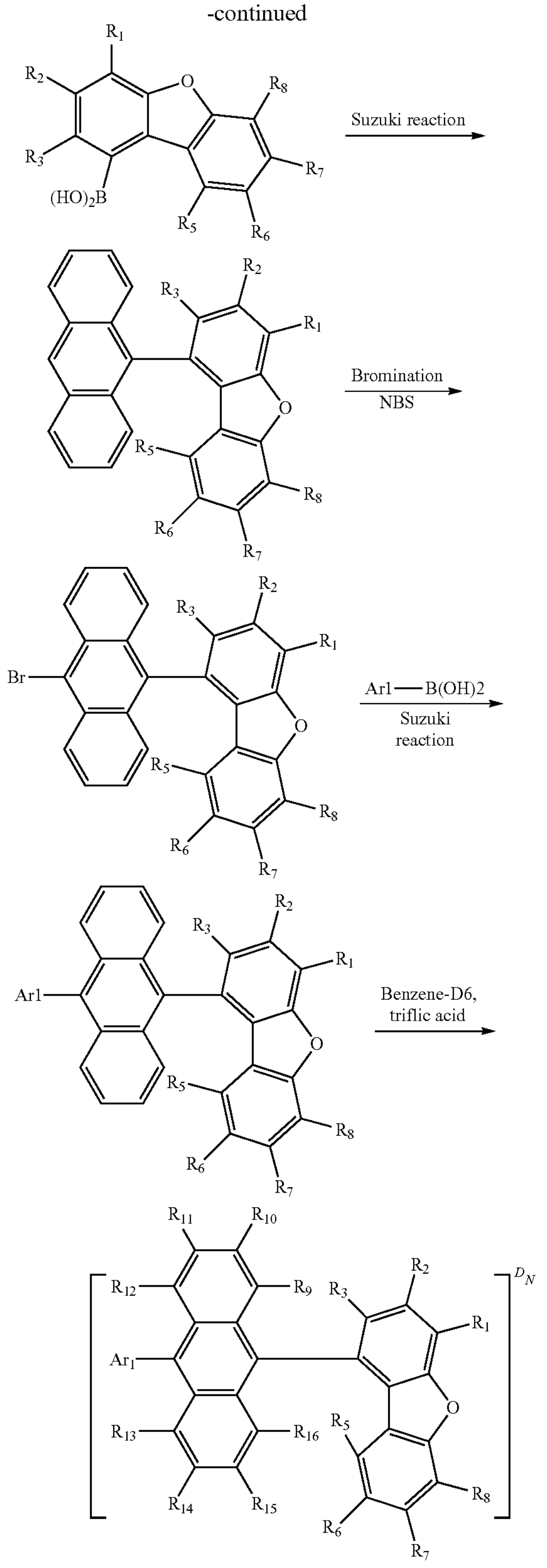
In reaction schemes 1 to 3, $Ar_1$, $R_1$ to $R_8$, $R_9$ to $R_{16}$, and $D_N$ are as defined in formula 1, and Hal represents a halogen.
In addition, the non-deuterated derivative of the compound represented by formula 1 may be prepared by a known coupling or substitution reaction. The deuterated derivative may be prepared by a similar method using a deuterated precursor material, or more generally, treating a non-deuterated compound with a deuterated solvent, D6-benzene, etc., in the presence of a Lewis acid such as aluminum trichloride or ethyl aluminum chloride, a H/D exchange catalyst such as trifluoromethanesulfonic acid or trifluoromethanesulfonic acid-D, etc. Further, the degree of deuteration may be controlled by varying reaction conditions such as reaction temperature. For example, by controlling reaction temperature and time, acid equivalent, etc., the number of N in formula 1 may be controlled.

Although illustrative synthesis examples of the compound represented by formula 1 were described above, one skilled in the art will be able to readily understand that all of them are based on a Buchwald-Hartwig cross-coupling reaction, an N-arylation reaction, a H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the above reactions proceed even when substituents, which are defined in formula 1 above but are not specified in the specific synthesis examples, are bonded.

The present disclosure provides an organic electroluminescent material comprising the organic electroluminescent compound represented by formula 1, and an organic electroluminescent device comprising the organic electroluminescent material. The material may consist of the organic electroluminescent compound according to the present disclosure alone, or may further comprise conventional materials included in the organic electroluminescent material.

The organic electroluminescent device according to the present disclosure comprises a first electrode, a second electrode, and at least one organic layer between the first and second electrodes, in which the organic layer may comprise at least one organic electroluminescent compound represented by formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

The second electrode may be a a transflective electrode or a reflective electrode, and the organic electroluminescent device may be a top emission type, a bottom emission type, or both-sides emission type according to the kinds of the material formed.

The first electrode and the second electrode may each be formed with a transmissive conductive material, a transflective conductive material, or a reflective conductive material. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

The organic electroluminescent compound represented by formula 1 of the present disclosure may be comprised in at least one of a light-emitting layer, a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer, preferably, may be comprised in a light-emitting layer. When used in the light-emitting layer, the organic electroluminescent compound represented by formula 1 of the present disclosure may be comprised as a host material. Preferably, the light-emitting layer may further comprise at least one dopant. If necessary, the organic electroluminescent compound of the present disclosure may be used as a co-host material. That is, the light-emitting layer may further include a compound other than the organic electroluminescent compound represented by formula 1 of the present disclosure (first host material) as a second host material. The weight ratio between the first host material and the second host material is in the range of 1:99 to 99:1.

The dopant comprised in the organic electroluminescent device of the present disclosure is at least one phosphorescent or fluorescent dopant, preferably at least one fluorescent dopant. The fluorescent dopant material applied to the organic electroluminescent device of the present disclosure is not particulary limited.

The organic layer may further comprise at least one compound selected from the group consisting of arylamine-based compounds and styrylarylamine-based compounds.

In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

The organic electroluminescent device of the present disclosure may emit white light by further including at least one light-emitting layer containing a blue, red, or green light-emitting compound, which is known in the art, besides the organic electroluminescent compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operation stability for the organic electroluminescent device. Preferably, the chalcogenide includes $SiO_x$ ($1 \le X \le 2$), $AlO_x$ ($1 \le X \le 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, or an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to prepare an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested in various structures such as a parallel side-by-side arrangement method, a stacking arrangement method, or CCM (color conversion material) method, etc., according to the arrangement of R (Red), G (Green), B (blue), or YG (yellowish green) light-emitting units. In addition, the organic electroluminescent material according to one embodiment of the present disclosure may also be applied to the organic electroluminescent device comprising a QD (quantum dot).

In order to form each layer of the organic electroluminescent device of the present disclosure, dry film-forming methods such as vacuum evaporation, sputtering, plasma, ion plating, etc., or wet film-forming methods such as ink jet printing, spin coating, dip coating, flow coating, etc., can be used.

When using a wet film-forming method, a thin film can be formed by dissolving or diffusing the materials forming each layer into any suitable solvent such as ethanol, chloroform, tetrahydrofuran, dioxane, etc. The solvent is not specifically limited as long as the material forming each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof, and the luminous property of the organic electroluminescent device comprising the same will be explained in detail with reference to the representative compounds of the present disclosure. However, the present disclosure is not limited to the following examples.

Example 1: Preparation of compound C-1

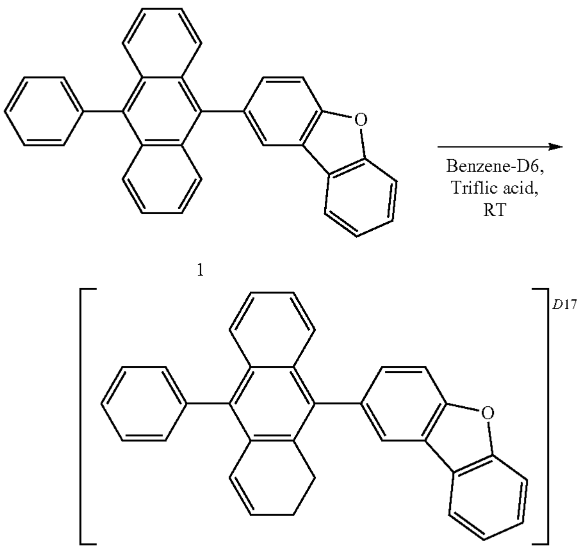

1

C-1

3.5 g of compound 1 (8.3 mmol) and 100 mL of benzene-D6 were introduced into a flask and heated to dissolve all of compound 1. After cooling the mixture to room temperature, 4.4 mL of triflic acid (49.8 mmol) was added thereto. After stirring the mixture at room temperature for 2 hours and 30 minutes, 20 mL of heavy water were added thereto. After stirring for 10 minutes, the mixture was neutralized with $K_3PO_4$ aqueous solution. An organic layer was extracted with dichloromethane, and the remaining moisture was removed using magnesium sulfate. The obtained organic layer was distilled under reduced pressure and separated by column chromatography to obtain 1.5 g of compound C-1

(yield: 41.3%). The number of deuteriums substituted was observed with molecular weight and NMR.

| MW | M.P. |
|---|---|
| 437.61 | 279.2° C. |

Device Example 1: Producing an OLED comprising a Compound according to the Present Disclosure An OLED comprising an organic electroluminescent compound according to the present disclosure was produced as follows: A transparent electrode indium tin oxide (ITO) thin film (10 Ω/sq) on a glass substrate for an OLED (GEOMATEC CO., LTD., Japan) was subjected to an ultrasonic washing with acetone, ethanol, and distilled water, sequentially, and then was stored in isopropanol. The ITO substrate was mounted on a substrate holder of a vacuum vapor deposition apparatus. Compound HI-1 was introduced into a cell of the vacuum vapor deposition apparatus, and the pressure in the chamber of the apparatus was then controlled to $10^{-6}$ torr. Thereafter, an electric current was applied to the cell to evaporate the above-introduced material, thereby forming a first hole injection layer having a thickness of 60 nm on the ITO substrate. Next, compound HI-2 was introduced into another cell of the vacuum vapor deposition apparatus and was evaporated by applying an electric current to the cell, thereby forming a second hole injection layer having a thickness of 5 nm on the first hole injection layer. Compound HT-1 was then introduced into another cell of the vacuum vapor deposition apparatus and was evaporated by applying an electric current to the cell, thereby forming a first hole transport layer having a thickness of 20 nm on the second hole injection layer. Compound HT-2 was then introduced into another cell of the vacuum vapor deposition apparatus and was evaporated by applying an electric current to the cell, thereby forming a second hole transport layer having a thickness of 5 nm on the first hole transport layer. After forming the hole injection layers and the hole transport layers, a light-emitting layer was formed thereon as follows: Compound C-1 was introduced into one cell of the vacuum vapor depositing apparatus as a host of the light-emitting layer, and compound BD was introduced into another cell as a dopant. The two materials were evaporated at different rates and the dopant was deposited in a doping amount of 2 wt % based on the total amount of the host and dopant to form a light-emitting layer having a thickness of 20 nm on the second hole transport layer. Next, compound ET-1 and compound EI-1 were evaporated at a rate of 1:1 in two other cells to deposit an electron transport layer having a thickness of 35 nm on the light-emitting layer. After depositing compound EI-1 as an electron injection layer having a thickness of 2 nm on the electron transport layer, an Al cathode having a thickness of 80 nm was deposited on the electron injection layer by another vacuum vapor deposition apparatus. Thus, an OLED was produced.

As a result, the minimum time taken to be reduced from 100% to 95% of the luminance at 2,000 nit was 76 hours.

Comparative Example 1: Producing an OLED comprising a Conventional Compound

An OLED was produced in the same manner as in Device Example 1, except that compound H-1 was used as the host material of the light-emitting layer.

As a result, the minimum time taken to be reduced from 100% to 95% of the luminance at 2,000 nit was 11 hours.

Comparative Example 2: Producing an OLED comprising a Conventional Compound

An OLED was produced in the same manner as in Device Example 1, except that compound H-2 was used as the host material of the light-emitting layer.

As a result, the minimum time taken to be reduced from 100% to 95% of the luminance at 2,000 nit was 25 hours.

Comparative Example 3: Producing an OLED comprising a Conventional Compound

An OLED was produced in the same manner as in Device Example 1, except that compound H-3 was used as the host material of the light-emitting layer.

As a result, the minimum time taken to be reduced from 100% to 95% of the luminance at 2,000 nit was 13 hours.

HI-1

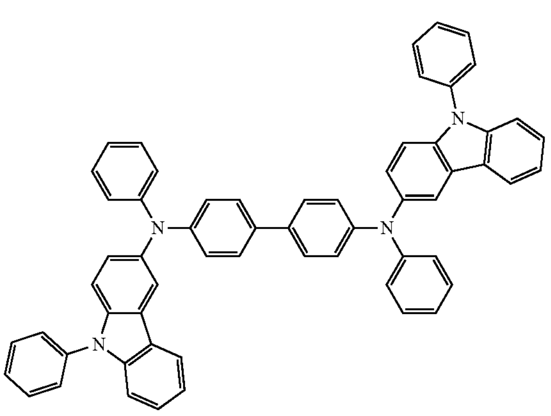

HI-2

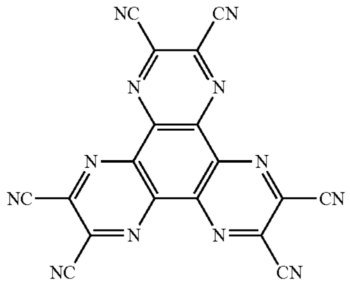

HT-1

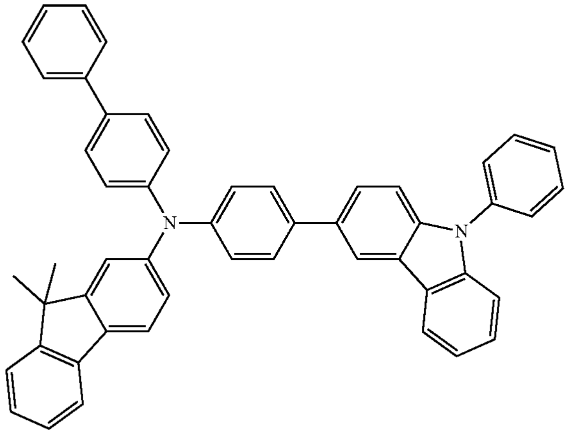

-continued

HT-2

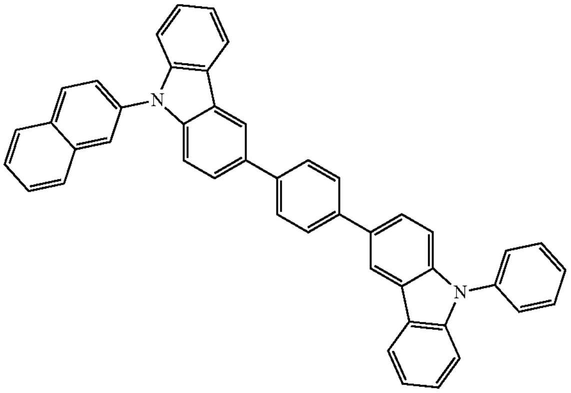

BD

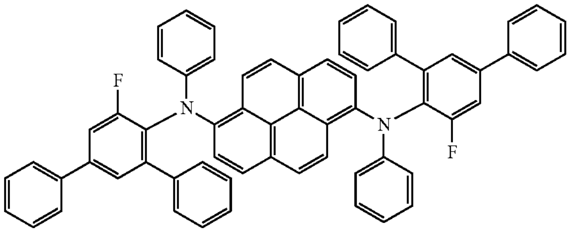

ET-1

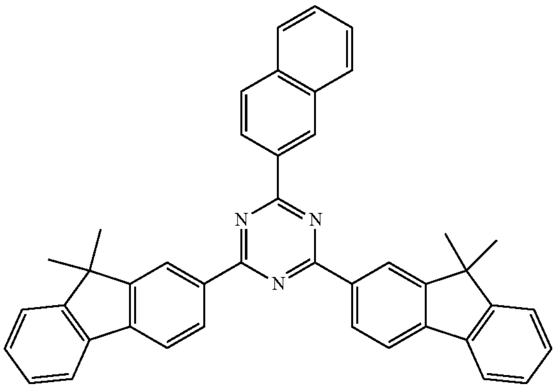

EI-1

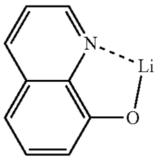

H-1

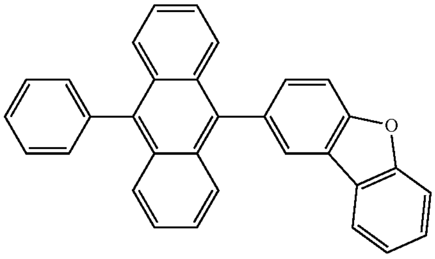

-continued

H-2

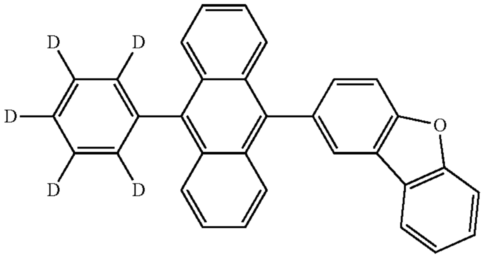

H-3

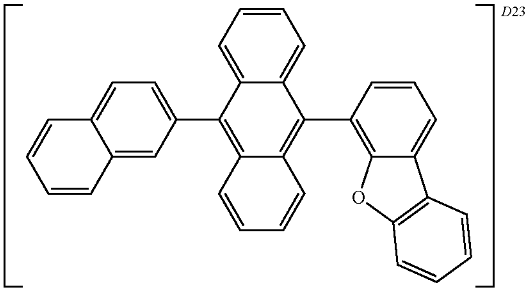

C-1

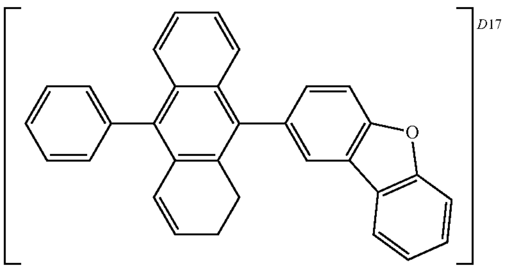

In the present disclosure, by producing an organic electroluminescent device by substituting hydrogens of the host compound of the light-emitting layer with deuterium, it can be seen that the lifespan characteristic is far superior to the organic electroluminescent device using conventional compounds as a host. It is understood that such improvement in lifespan characteristic of an OLED is due to an improvement of stability of the material due to decrease of the zero point vibration energy of the deuterated compound, compared to a compound which is non-deuterated or deuterated with less deuterium. In addition, without intending to be limited by theory, in order to improve the lifespan of the blue light-emitting fluorescent organic electroluminescent device, the electron mobility needs to be controlled, and since dibenzofuran has faster hole mobility than aryls, a similar effect to a decrease of the electron mobility can be obtained. Without intending to be limited by theory, a decrease in electron mobility can lead to a decrease of degradation of adjacent layers, thereby increasing lifespan. In the aspect of such effect, deuterating a compound wherein an anthracene is substituted with dibenzofuran may be advantageous compared to deuterating a compound wherein an anthracene is substituted with an aryl.

The invention claimed is:

1. An organic electroluminescent compound represented by the following formula 1-3:

(1-3)

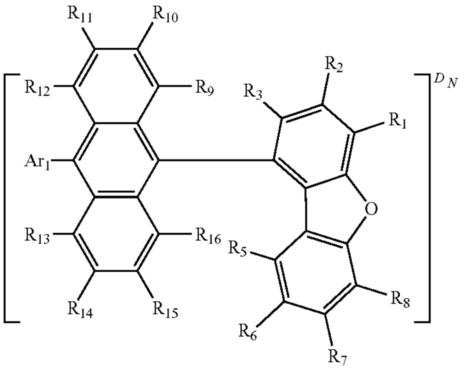

wherein $R_1$ to $R_3$, $R_5$ to $R_6$, and $R_8$ each represent hydrogen;

$R_9$ to $R_{16}$ each independently represent hydrogen or deuterium;

$R_7$ represents a phenyl substituted with deuterium or a biphenyl substituted with deuterium;

$Ar_1$ represents a phenyl substituted with deuterium or a biphenyl substituted with deuterium;

$D_N$ means that N hydrogen atoms are substituted with deuterium; and

N represents an integer of 8 to 26.

2. The organic electroluminescent compound according to claim 1, wherein N represents an integer of 13 to 26.

3. An organic electroluminescent material comprising the organic electroluminescent compound according to claim 1.

4. An organic electroluminescent device comprising the organic electroluminescent compound according to claim 1.

5. The organic electroluminescent device according to claim 4, wherein the organic electroluminescent compound is comprised in a light-emitting layer.

* * * * *